United States Patent [19]

Ellard

[11] Patent Number: 5,007,903
[45] Date of Patent: Apr. 16, 1991

[54] SYRINGE ADAPTED TO PREVENT NEEDLE STICKS

[75] Inventor: Terence R. Ellard, Seattle, Wash.

[73] Assignee: Real World Design & Development Company, Seattle, Wash.

[21] Appl. No.: 274,817

[22] Filed: Nov. 22, 1988

[51] Int. Cl.⁵ ............................................. A61M 5/32
[52] U.S. Cl. ................................. 604/195; 604/110; 604/220; 604/196
[58] Field of Search ............... 604/110, 192, 263, 195, 604/194, 196, 197, 198, 228, 218, 220

[56] References Cited

U.S. PATENT DOCUMENTS

| | | | |
|---|---|---|---|
| 2,841,144 | 7/1958 | Cohen | 604/198 |
| 3,459,339 | 8/1969 | Damgaard | 604/208 |
| 4,492,576 | 1/1985 | Dragan | 433/90 |
| 4,553,962 | 11/1985 | Brunet | 604/198 |
| 4,713,056 | 12/1987 | Butterfield | 604/110 |
| 4,715,854 | 12/1987 | Vaillancourt | 604/191 |
| 4,747,829 | 5/1988 | Jacob et al. | 604/110 |
| 4,747,830 | 5/1988 | Gloyer et al. | 604/110 |
| 4,790,822 | 12/1988 | Haining | 604/110 |
| 4,861,338 | 8/1989 | Mathiesen et al. | 604/110 |
| 4,863,427 | 9/1989 | Cocchi | 604/110 |
| 4,915,692 | 4/1990 | Verlier | 604/110 |
| 4,915,699 | 4/1990 | Kornberg | 604/195 |
| 4,932,945 | 6/1990 | Braginetz et al. | 604/195 |
| 4,955,869 | 9/1990 | Bin | 604/195 |

FOREIGN PATENT DOCUMENTS

| | | | |
|---|---|---|---|
| 1126718 | 11/1956 | France | 604/218 |
| 394498 | 11/1965 | Switzerland | 604/196 |

*Primary Examiner*—Stephen C. Pellegrino
*Assistant Examiner*—Mark O. Polutta
*Attorney, Agent, or Firm*—Graybeal, Jensen & Puntigam

[57] ABSTRACT

The syringe includes a barrel (12) and first and second piston-like elements (16,18) which are adapted for fluid tight movement therein, wherein the first and second pistons (16,18) are connected by a flexible, thin cord (36). A hollow needle (28) is mounted on and extends from the front surface (24) of the first piston (16). The needle (28) communicates with the space between the first and second pistons (16,18). A plunger (32) is attached to the rear surface (31) of the second piston (18) and extends from the rear of the syringe in conventional fashion. In the forwardmost position of the first piston (16), the needle (28) extends outwardly from the front end of the syringe barrel (12) but in the rearmost position, the needle (28) is within the barrel (12).

14 Claims, 2 Drawing Sheets

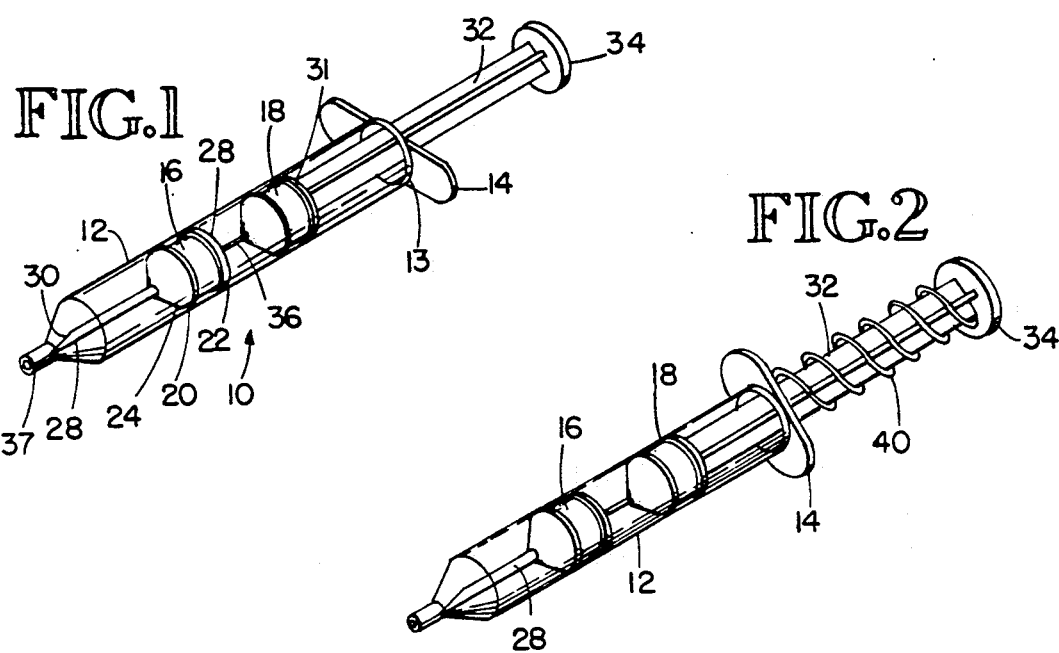
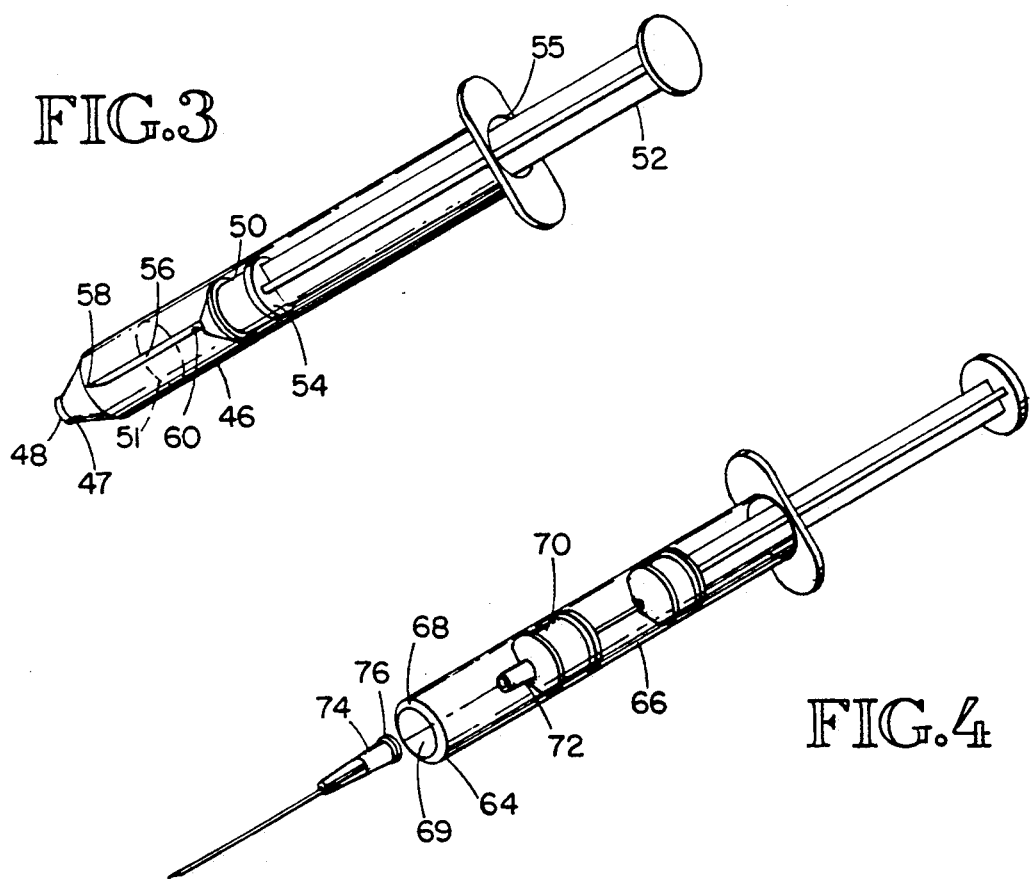

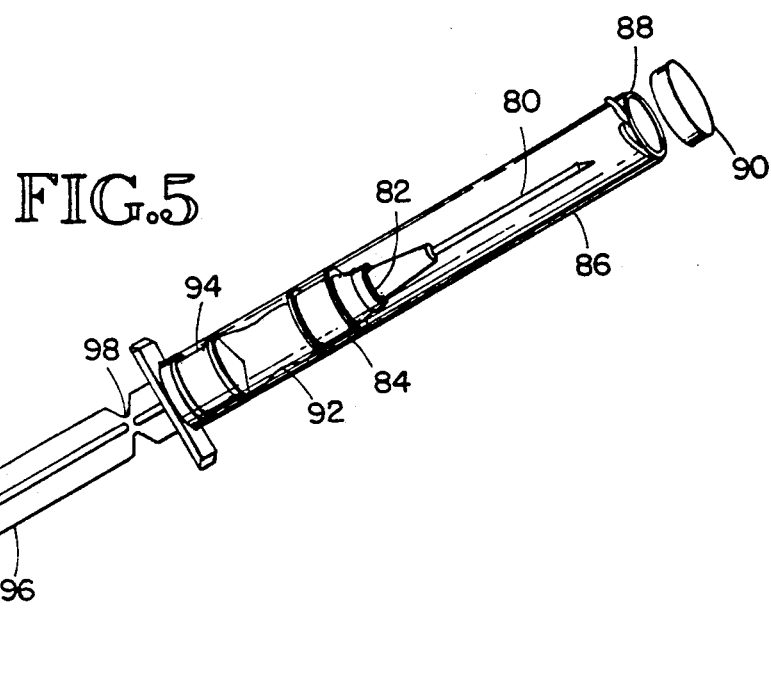
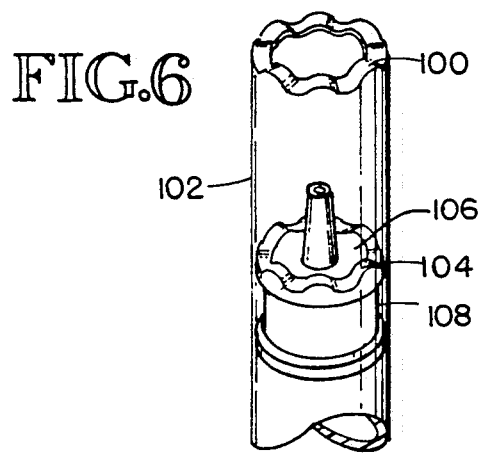
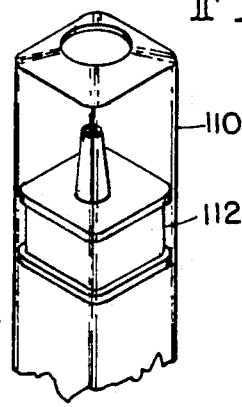
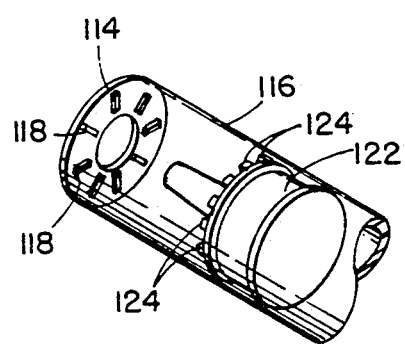

SYRINGE ADAPTED TO PREVENT NEEDLE STICKS

DESCRIPTION

1. Technical Field

This invention relates generally to the syringe art, and more specifically concerns a syringe which is constructed to permit a needle portion thereof to be selectively retracted into a barrel portion.

2. Background Art

Conventional syringes, including hypodermic as well as other types of syringes, typically have fixed needles which protrude forwardly from the end of the syringe barrel. In a hypodermic syringe, the barrel contains the medication used in an injection. In transport of the syringe, and in storage prior to actual use, syringe needles are typically protected in some fashion, such as by an elongated plastic cap which fits around the needle. Further, the entire syringe is sometimes encased in a paper or plastic container. These packaging techniques insure the sterility of the syringe, but also serve to protect the clinician or other user of the syringe from accidentally getting nicked or pricked by the syringe needle, a result generally referred to as a needle "stick".

In the past, needle sticks have been inconvenient and have caused some discomfort. Risk of infection, such as for hepatitis, has in the past caused some concern. However, recently, with the incidence of the AIDS virus, and in particular the severity of the effects thereof, and the knowledge that the virus can be transmitted by needles, there has arisen an extraordinary concern over the possibility of needle sticks. The present invention greatly reduces the possibility of such needle sticks.

Disclosure of the Invention

The syringe of the present invention includes a syringe barrel, and first and second elements positioned in a spaced relationship within the barrel, the first element being forward of the second element, wherein the first and second elements are adapted for fluid tight movement in the barrel. The syringe also includes a hollow needle which extends from the front end of the first element and is in communication with the space between the first and second elements, wherein the needle extends outwardly from the front end of the barrel when the first element is in its forwardmost position within the barrel. A plunger is attached to the rear element, wherein the plunger extends rearwardly from the rear end of the barrel. Means connect the first and second elements within the barrel in such a manner that when the first and second elements are in a first relationship relative to each other, forward movement of the second element results in forward movement of the first element, and when the first and second elements are in a second relationship relative to each other, rearward movement of the second element results in rearward movement of the first element, and wherein the connecting means is arranged such that the second element can move over a selected distance without moving the first element, when the first and second elements are not in said first or second relationship.

BRIEF DESCRIPTION OF THE DRAWINGS

FIG. 1 is an isometric view of a first embodiment of the article of the present invention.

FIG. 2 is an isometric view of a modified version of the article of FIG. 1.

FIG. 3 is an isometric view of a second embodiment of the article of the present invention.

FIG. 4 is an isometric view showing one additional feature which can be incorporated in the article of FIGS. 1–3.

FIG. 5 is an isometric view showing several additional features which can be incorporated in the articles of FIGS. 1–3.

FIG. 6 is an isometric view of a further feature which can be incorporated in the articles of FIGS. 1–3.

FIG. 7 is an isometric view showing a second embodiment of the feature of FIG. 6.

FIG. 8 is an isometric view showing a third embodiment of the feature of FIGS. 7 and 8.

BEST MODE FOR CARRYING OUT THE INVENTION

FIG. 1 shows a first embodiment of the article of the present invention, which is directed toward a syringe having a retractable needle so as to minimize the opportunity for needle sticks during transportation and handling of the syringe. The syringe 10 includes a conventional barrel 12 which can be of different lengths and diameters, depending upon the desired capacity of the syringe. In one example, for a three CC capacity syringe, the barrel is approximately 2¾ inches long with a diameter of approximately ⅜ inch. At the rear end 13 of the barrel 12 is a flat, narrow projection 14 which extends outwardly at right angles to the barrel 12. Projection 14 serves as a base for support of the fingers during use of the syringe 10.

In the embodiment of FIG. 1, two piston-like elements 16 and 18 are positioned within the barrel 12. Each piston-like element comprises a rubber or plastic cylinder having circumferential lips 20 and 22 (element 16) at the front and rear ends thereof. The diameter of the lips 20 and 22 is such as to provide a fluid tight seal between the piston elements 16 and 18 and the interior surface of the barrel 12. In the embodiment shown, the distance between the respective lips 20 and 22 on each piston element is approximately 5/16 inch. In another embodiment, one lip is used on each element. It is important, however, that a fluid-tight seal be maintained.

The front surface 24 of each piston-like element 16, 18 is somewhat conical in shape, while the rear surface 26 is shaped inversely conical. Extending from the front surface 24 of the forward piston element 16, approximately central thereof, is a conventional syringe needle 28. The needle 28 is hollow, i.e. it has an opening down the center thereof, with the opening communicating between the tip 30 of the needle 28 and the rear end thereof which terminates at the rear surface of the forward piston 16, so that there is fluid communication between the tip of the needle and the space between the forward piston 16 and the rear piston 18.

Affixed to the rear surface 31 of the rear piston element 18 and extending out the rear end of the barrel 12 is a syringe plunger 32. The plunger conventionally is X-shaped in cross-section and includes a small, thin plunger head 34 at the rear end of the plunger 32.

Connecting the two piston elements 16 and 18 in the embodiment shown is a length of thin cord 36. The length of the cord 36 determines the useful medicant capacity of the syringe. For the above described syringe, a cord approximately 1 inch long results in a syringe capacity of 1½ CCs. As described hereinafter, alternatives to a cord are possible; however, it is important that the cord or other element be flexible and otherwise configured and arranged so that most if not all of the medicant between the two elements is expelled during operation of the syringe.

In use of the embodiment of FIG. 1, the plunger 22 is first pushed all the way forward such that the front surface 24 of the forward piston 16 is at the front end of the syringe, with the needle 28 as a result protruding beyond the very front end 37 of the barrel 12. In this position, the needle 28 is inserted into a vial (not shown) of medicant, and the plunger 32 is drawn rearwardly permitting the medicant to enter the increasing space between the forward and rear piston elements. When the cord 36 becomes taunt, the syringe is full. The forward piston 16 is still in position at the front end of the barrel 12. The needle is then removed from the medicant vial and is ready for use.

In the injection process, after the needle has been set in the patient, the plunger 32 is pushed forwardly, forcing the medicant in the space between the two piston elements 16, 18 out the tip of the needle 28 into the patient. When the ejection is complete, the barrel is typically held in place and the plunger 32 is pulled all the way to the rear, in turn pulling both pistons rearwardly and the needle 28 out of the patient and back into the barrel, without at any time exposing the tip of the needle.

The embodiment of FIG. 2 is similar to that of FIG. 1, except that it includes a spring 40 which is positioned along and around the plunger 32 between projection 14 at the rear end of the barrel 12 and the head 34 at the rear end of plunger 32. The use of the spring results in the automatic filling of the syringe (when the needle has been inserted into a vial) after the piston elements are moved to their most forward position in the barrel by forward pressure on the plunger against the action of the spring. When the forward pressure is released from the plunger, the action of the spring forces the plunger, and hence the rear piston element 18, backwardly, resulting in medicant filling the space between the two piston elements. Likewise, when the injection is completed, release of pressure on the plunger permits the spring to draw the two piston elements and the needle back into the barrel. It should be understood that other means could be used to accomplish the same result as a spring, for instance, a resilient band, i.e. a rubber band, or perhaps a vacuum arrangement in the barrel to the rear of the rear piston.

FIG. 3 shows another embodiment of the present invention. This embodiment includes a conventional syringe barrel 46 similar to that of FIG. 1, except that at the front end 47 thereof is positioned a self-sealing rubber membrane 48, which has the capability of sealing itself against fluid leakage following penetration and then removal of a syringe needle. The article of FIG. 3 includes a single piston element 50, similar to piston elements 16 or 18 shown in FIGS. 1 and 2. A plunger 52 extends rearwardly in the barrel 46 from the rear surface 54 of the piston 50 and outwardly from the rear end 55 of the barrel.

Extending forwardly from the front surface of the single piston-like element 50 is a needle 56. The needle includes a conventional longitudinal interior opening (not shown) connecting the tip 58 of the needle 56 and an opening 60 which extends through the side surface of the needle 56 at a point just forward of the front surface of the piston element.

In use, the plunger 52 is initially pushed into the barrel 46 until the piston element 50 is at its forwardmost position in the barrel 46, at which point the needle 56 extends through the membrane 48 and outwardly therefrom. For use in giving injections, the needle 56 is first inserted in a vial of medicant, and the plunger 52 is then moved rearwardly, such that the increasing volume in the barrel 46 between the front end 47 thereof and the piston element 50 fills with medicant. The needle 56 will of course be gradually retracting during this process. When sufficient medicant has been obtained (typically the tip of the needle 56 still protrudes beyond the membrane 48) the needle is removed from the vial and then injected into the patient (usually this will be a muscular or transcutaneous injection). The plunger 52 is then moved forwardly, which simultaneously results in the needle 56 moving forwardly and the medicant being forced from the tip of the needle into the site of the injection. When the injection is complete, the needle is removed, typically by retracting the plunger while the syringe is held stationary, thereby retracting the needle from the patient into the barrel without exposing the needle.

The embodiment of FIG. 3 can also be used as shown to obtain blood specimens. This is done by inserting the tip of the protruding needle 56 into a vein and then holding the needle 56 stationary while moving the barrel 46 forwardly to the surface of the skin. The embodiment of FIG. 3 can be also slightly modified to provide a removable capsule within the syringe for fluid specimens such as blood. In such an embodiment, a second sealing membrane, shown representationally by the dotted line 51 in FIG. 3, could be positioned interiorly of the barrel 46, a selected distance from the front end thereof, but forwardly of the piston element 50. The needle 56 would have to be long enough so that it extends a considerable distance outwardly from the front end of the barrel 46 when the piston element 50 is adjacent the second membrane 51. The needle is then inserted in the vein or artery of the patient. Blood is then withdrawn from the patient, as explained above, with the blood moving into the space within the barrel 46 between the two sealing membranes. The barrel is constructed so that the front part thereof, bounded by the two sealing membranes, could be removed from the remainder thereof. The needle 56 would be removed through the rear membrane, which seals upon exit of the needle. The portion of the barrel, i.e. the capsule, containing the fluid specimen is convenient to store and otherwise handle.

FIGS. 4 and 5 show additional features which can be incorporated in the articles of FIGS. 1-3. In FIG. 4, the front end 64 of the barrel 66 of the syringe is cut off, leaving a beveled barrel front edge 68 and a fairly large opening 69. The front surface of the forward piston element 70 includes a small cylindrical mounting stub 72. A detachable needle 74 may be fitted or locked to the mounting stub. The detachable needle 74 is of conventional configuration and is available from several commercial sources. The needle includes a base portion 76 which is adapted to permit a "slip fit" connection between the needle base 76 and the mounting stub 72 on piston element 70.

FIG. 5 shows further features which can be used with the various embodiments of the present invention. This includes a Luer Lock type connection between a detachable needle 80 and a mounting element 82 at the front of forward piston 84, which is positioned within syringe barrel 86. In a Luer Lock type connection, the configuration of the base portion of the needle 80 and the mounting element 82 is such that the needle must be turned through a small angle in order to lock and unlock the needle relative to the mounting element. The front end 88 of barrel 86 and the outer surface thereof are configured to accept a cap 90 which can be screwed onto the end of the barrel 86, thereby providing protection for the needle and to seal the syringe for shipping, thereby eliminating the need for separate packaging.

The embodiment of FIG. 5 also includes a somewhat different element 92 which connects the forward piston 84 with the rear piston 94. Connector 92 is a thin sheet of molded flexible material, such as a flexible plastic, which provides the same function as the thin cord or string shown in the embodiment of FIGS. 1 and 2. The sheet does need to be relatively thin to prevent the two pistons from separating due to the action of the connector. In addition, there are still other ways of connecting the two pistons. For instance, the connector could be one or more thin ribbons of flexible material or the connector could be a solid element having a slidable relationship with the rear piston over a selected distance. What is desirable in all cases, however, is that the rear piston be movable over a selected distance relative to the front piston but in addition is so connected to the forward piston that it can move up to the forward piston sufficiently close so that all of the fluid between the two pistons is expelled and so that it can move the forward piston to the front of the barrel in one relationship and can move the forward piston rearwardly in another relationship, under action of the plunger.

Referring still to FIG. 5, the plunger 96 of the syringe is notched at 98 so that the rear portion of the plunger can be conveniently broken off, thereby preventing further use of the syringe as well as reemergence of the needle due to accidental action of the plunger.

In a still further consideration, it is desirable to have the rear surface of the forward piston configured so that any air bubbles in the fluid between the two pistons are guided to the opening in the rear end of the needle.

It should be understood that all of the features described above with respect to FIGS. 4 and 5 can be used with the embodiments of FIG. 1-3.

FIGS. 6-8 show three different embodiments used generally to prevent the forward piston from turning or rotating within the barrel of the syringe during the changing of detachable needles, in particular, the Luer Lock configuration. FIG. 6 shows one embodiment. In this embodiment, the front end edge 100 of the barrel 102 of the syringe is convoluted on the interior surface thereof. Matching convolutions 104 are provided at the peripheral edge of the front surface 106 of the forward piston 108. When the forward piston 108 is in its forwardmost position, the convoluted surface 104 of the forward piston 108 will mate with the convoluted interior front end edge 100 of the barrel, thereby preventing any rotational movement of the forward piston 108, when a needle is being attached or detached to the forward piston.

The embodiment of FIG. 7 includes a barrel 110 which has a particular configuration, somewhat square in outline, with rounded corners. The forward piston 112 has the same configuration, thereby again preventing rotational movement of the forward piston.

In the embodiment of FIG. 8, the interior surface of the forward end edge 114 of the barrel 116 has a series of projections 118 which extend a small distance into the interior of the barrel 116. The front surface of the forward piston 122 includes valleys or grooves 124 therein which mate with the projections 118 when the piston 122 is in its forwardmost position, again preventing rotational movement of the piston.

Although a preferred embodiment of the invention has been disclosed herein for purposes of illustration, it should be understood that various changes, modifications and substitutions may be incorporated in such embodiment without departing from the spirit of the invention as defined by the claims which follow.

I claim:

1. An improved syringe, comprising:
   a syringe barrel;
   a first, forward piston member and a second rear piston member, said first and second piston members being positioned in succession within the syringe barrel and adapted for fluid-tight movement therein;
   a hollow needle extending from the front end of the first piston member and in fluid communications with the space between the first and second piston members, wherein said needle extends outwardly from the front end of the barrel when the first piston member is in its forwardmost position within the barrel;
   a plunger attached to the second piston member, the plunger extending from the rear end of the barrel;
   a connecting member, independent of the needle and the barrel, extending between the first and second piston members and connected thereto, wherein said connecting member is positioned within the barrel and is collapsible such that when the first and second piston members are in a first relationship relative to each other, forward movement of the second piston member results in forward movement of the first piston member and such that when the first and second piston members are in a second relationship relative to each other, rearward movement of the second piston member results in rearward movement of said first piston member and such that the second piston member can move a selected distance toward and away from the first piston member within the barrel without moving the first piston member when the first and second piston members are not in said first or second relationship.

2. An article of claim 1, wherein the first and second piston members are cylindrical in configuration, having at least one relatively narrow circumferential lip extending radially outwardly therefrom, in fluid-tight sealing contact with the interior surface of the barrel.

3. An article of claim 1, wherein the connecting member is a thin, thread-like element connecting the first and second piston members.

4. An article of claim 1, wherein the connecting member is a thin, flexible relatively wide connector.

5. An article of claim 1, including a resilient element operative to bias the plunger and hence the first and second piston members and the needle in a position wherein the needle is retracted within the barrel.

6. An article of claim 1, wherein the length of the connecting member is sufficiently long that a desired amount of fluid can be accommodated in the space between the first and second piston members.

7. An article of claim 1, wherein the needle is detachable from the first piston member.

8. An article of claim 1, including a cap means adapted for closing the front end of the barrel.

9. An article of claim 1, wherein the plunger includes a narrowed portion at a point along its length to facilitate the breaking of the plunger, so as to prevent further use of the syringe.

10. An article of claim 1, including means to prevent the rotation of the first piston member when it is in a forward position within the barrel.

11. An article of claim 10, wherein the rotation preventing means includes a plurality of projections extending inwardly of the barrel from the interior of the front end edge thereof and a mating configuration on the front surface of the first piston member.

12. An article of claim 10, wherein the rotation preventing means includes the barrel configured in a non-circular cross-section relative to the first piston member such as to prevent rotation of the first piston member.

13. An article of claim 1, wherein said syringe barrel is a single unitary element.

14. An article of claim 1, wherein said needle is at all times in fluid communication with the space between the first and second piston members.

* * * * *